(12) United States Patent
Paschalis et al.

(10) Patent No.: US 9,999,553 B2
(45) Date of Patent: Jun. 19, 2018

(54) MATERIALS AND METHODS FOR OIL REMOVAL

(71) Applicant: Massachusetts Eye and Ear Infirmary, Boston, MA (US)

(72) Inventors: Eleftherios Ilios Paschalis, Quincy, MA (US); Demetrios Vavvas, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 259 days.

(21) Appl. No.: 14/850,537

(22) Filed: Sep. 10, 2015

(65) Prior Publication Data

US 2016/0354198 A1 Dec. 8, 2016

Related U.S. Application Data

(60) Provisional application No. 62/048,671, filed on Sep. 10, 2014.

(51) Int. Cl.
| | | |
|---|---|---|
| *B01J 20/283* | (2006.01) | |
| *C02F 1/28* | (2006.01) | |
| *C08B 1/00* | (2006.01) | |
| *C08G 77/00* | (2006.01) | |
| *A61F 13/36* | (2006.01) | |
| *B01J 20/26* | (2006.01) | |
| *B01J 20/24* | (2006.01) | |
| *B01J 20/08* | (2006.01) | |
| *B01J 20/28* | (2006.01) | |
| *B01J 20/32* | (2006.01) | |
| *C08G 77/04* | (2006.01) | |

(Continued)

(52) U.S. Cl.
CPC ............ *A61F 13/36* (2013.01); *B01J 20/08* (2013.01); *B01J 20/24* (2013.01); *B01J 20/262* (2013.01); *B01J 20/28023* (2013.01); *B01J 20/28085* (2013.01); *B01J 20/3236* (2013.01); *C02F 1/281* (2013.01); *C02F 1/285* (2013.01); *C02F 1/286* (2013.01); *C02F 1/288* (2013.01); *C08G 77/04* (2013.01); *C08L 83/04* (2013.01); *C02F 2101/32* (2013.01); *C02F 2103/007* (2013.01)

(58) Field of Classification Search
None
See application file for complete search history.

(56) References Cited

U.S. PATENT DOCUMENTS

2011/0111178 A1* 5/2011 Wind .................. C08J 7/123
428/170
2012/0070878 A1* 3/2012 Fink .................. B01L 3/502707
435/243

OTHER PUBLICATIONS

Apple et al., "Irreversible silicone oil adhesion to silicone intraocular lenses. A clinicopathologic analysis," OPHTHA, 1996, 103(10):1555-1561.

(Continued)

*Primary Examiner* — Clare M Perrin
(74) *Attorney, Agent, or Firm* — Fish & Richardson P.C.; Vasily A. Ignatenko

(57) ABSTRACT

Provided herein is an oleophilic matrix comprising at least one polymer selected from the group consisting of a polydimethylsiloxane having micropillars; a microporous polydimethylsiloxane; and an ophthalmic-grade cellulose having an alumina-deposited surface. The matrixes can be used, for example, to remove an oil, such as a silicone oil, e.g., from a hydrophobic surface such as an intraocular lens, or from an aqueous environment.

19 Claims, 14 Drawing Sheets
(11 of 14 Drawing Sheet(s) Filed in Color)

(51) Int. Cl.
*C08L 83/04* (2006.01)
*B01J 20/00* (2006.01)
*B01D 39/00* (2006.01)
*C02F 101/32* (2006.01)
*C02F 103/00* (2006.01)

(56) References Cited

OTHER PUBLICATIONS

Apple et al., "Silicone oil adhesion to intraocular lenses: an experimental study comparing various biomaterials," J. Cartaract & Refrative Surgery, 1997, 23(4):536-544.
Dong et al., "Reinforcement of electrospun membranes using nanoscale Al2O3 whiskers for improved tissue scaffolds," J Biomed Mater Res A, 2012, 100A(4):903-910.
Finch et al., "Biocompatibility of atomic layer-deposited alumina thin films," J. Biomed Mater Res A, 2008, 87(1):100-106.
Fischer et al., "Surface-modified silicone foils for intraocular implantation," Graefes Arch Clin Exp Ophthalmol, 2012, 250(6):823-827.
Ignjatovic et al., "Injectable polydimethylsiloxane-hydroxyapatite composite cement," Biomed Mater Eng, 2003, 13(4):401-410.
Kido et al., "Biocompatibility of a porous alumina ceramic scaffold coated with hydroxyapatite and bioglass," J. Biomed Mater Res A, 2013, 102(7):2072-2078.
Kusaka et al., "Condensation of silicone oil on the posterior surface of a silicone intraocular lens during vitrectomy," AJOPHT, 1996, 121(5):574-575.
Lachhman et al., "Multi-layered poly-dimethylsiloxane as a non-hermetic packaging material for medical MEMS," Conf Proc IEEE Eng Med Biol Soc, 2012, 2012:1655-1658.
Langefeld et al., "A new way of removing silicone oil from the surface of silicone intraocular lenses," Graefes Arch Clin Exp Ophthalmol, 1999, 237(3):201-206.
Lee et al., "Mechanisms for hydrophilic/hydrophobic wetting transitions on cellulose cotton fibers coated using Al2O3 atomic layer deposition," J. Vac Sci Technol A, 2012, 30(1):1A163.
Ogihara et al., "Biocompatibility and bone tissue compatibility of alumina ceramics reinforced with carbon nanotubes," Nanomedicine, 2012, 7(7):981-993.
Paschalis et al., "A Novel Implantable Glaucoma Valve Using Ferrofluid," PLoS One, 2013, 8(6):e67404.
Stappler et al., "F4H5: a novel substance for the removal of silicone oil from intraocular lenses," British J. Ophthalmology, 2010, 94(3):364-367.
Stolba et al., "Intraocular silicone lenses in silicone oil: an experimental study," Graefes Arch Clin Exp Ophthalmol, 1996, 234(1):55-57.
Walter et al., "Development of a completely encapsulated intraocular pressure sensor," Ophthalmic Res, 2000, 32(6):278-284.
Williams et al., "Characterization of a novel active release coating to prevent biofilm implant-related infections," J Biomedical Materials Research Part B: Applied Biomaterials, 2013, 101B(6):1078-1089.
Williams et al., "Novel Heavy Tamponade for Vitreoretinal Surgery," Invest Ophthalmol Vis Sci, 2013, 54(12):7284-7292.

* cited by examiner

MATERIALS AND METHODS FOR OIL REMOVAL

CLAIM OF PRIORITY

This application claims the benefit of U.S. Provisional Application No. 62/048,671, filed Sep. 10, 2014. The entire contents of the foregoing are hereby incorporated by reference.

TECHNICAL FIELD

This invention relates to materials and methods for the removal of oil.

BACKGROUND

Silicone oil (SiO) adherence on intraocular lenses (IOL) is a well-known complication of vitreoretinal surgery. Remnants of SiO in the eye can form droplets, strongly adherent to the surface of the IOL, that cause visual acuity reduction and induction of high order refractive aberrations, monocular diplopia, glare and halos. Removal of such droplets is technically challenging due to the strong hydrophobic interaction between the oil and the lens. This complication is more frequent with hydrophobic IOLs, including silicone IOLs and polymethylmethacrylate IOLs.

Over the past years, several methods have been advocated to remove SiO from IOLs using solvents or viscoelastics. However, solvents may cause tissue toxicity, and viscoelastic compounds often result in inadequate removal. Currently, the surgical explantation and replacement of the IOL is the mainstay of treatment, but it is associated with increase in surgical time, complication rate, and cost.

SUMMARY

At least in part, the present invention is based on the development of oleophilic matrices for adsorption of an oil, such as a silicone oil, e.g., from a hydrophobic surface such as an intraocular lens, or from an aqueous environment.

Provided herein are oleophilic matrices comprising at least one polymer selected from the group consisting of a polydimethylsiloxane having micropillars; a microporous polydimethylsiloxane; and an ophthalmic-grade cellulose having an alumina-deposited surface.

In some embodiments, the polymer is a polydimethylsiloxane having micropillars. In some embodiments, the micropillars have a size in a range from about 0.5 µm to about 120 µm. In some embodiments, the micropillars have a size of about 10 µm. In some embodiments, the micropillars have a size of about 40 µm. In some embodiments, the micropillars have a size of about 80 µm. In some embodiments, the micropillars have a size of about 120 µm.

In some embodiments, the polymer is a microporous polydimethylsiloxane. In some embodiments, the micropores have a size in a range from about 0.5 µm to about 500 µm. In some embodiments, the micropores have a size of about 100 µm. In some embodiments, the micropores have a size of about 200 µm. In some embodiments, the micropores have a size of about 300 µm.

In some embodiments, the polymer is an ophthalmic-grade cellulose having an alumina-deposited surface. In some embodiments, the alumina-deposited surface was formed by atomic layer deposition. In some embodiments, the alumina-deposited surface has a thickness in a range from about 2 to about 14 angstroms.

Also provided herein are methods for removing an oil from an intraocular lens, comprising contacting the oil with an oleophilic matrix as described herein; absorbing the oil onto the oleophilic matrix; and withdrawing the oleophilic matrix to remove the oil from the intraocular lens. In some embodiments, contacting the oil with an oleophilic matrix comprises using a swab having a tip portion and a rigid member, wherein the tip portion of the swab comprises the oleophilic matrix. In some embodiments, the oil is a silicone oil.

Also provided herein is a method for removing an oil from an aqueous medium, comprising contacting the oil with an oleophilic matrix as described herein; absorbing the oil onto the oleophilic matrix; and withdrawing the oleophilic matrix to remove the oil from the aqueous medium. In some embodiments, the aqueous medium is a naturally-occurring or man-made body of water.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the following description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 1A shows macroscopic appearance of the Micro-patterned PDMS material with pillar dimensions 10×10×25 µm (width×length×height) and pillar spacing of 10 µm. FIG. 1B shows top-view graphical representation of the surface of a micro-patterned PDMS with nano roughness. The surface roughness is constructed by 600×600 nm features on the surface of each micro pillar (graphical representation not to scale). FIG. 1C shows projection view of the pillars. FIG. 1D shows graphical representation of a water droplet, at Cassie-Baxter state, resting on the surface of the micro-patterned PDMS. FIG. 1E shows macroscopic appearance of 3-D porous PDMS material. FIG. 1F shows graphical representation of water-soluble particles arranged on a substrate prior to PDMS filling. FIG. 1G shows PDMS curing and particle removing using water. FIG. 1H shows removal of the particles results to a 3-D interconnected porous PDMS block, as shown by the x-ray micro-computed tomography. 3-D porosity diameter between 100 and 300 The 3-D surface roughness provides further surface energy reduction (hydrophobicity) and increase oleophilicity. The 3-D structure facilitates SiO absorption within the material. FIG. 1I shows macroscopic appearance of modified ALD Weck-Cel. FIG. 1J shows photos of Non-modified Weck-Cel® submerged in water. FIG. 1K shows ALD modified Weck-Cel® submerged in water. FIG. 1L shows significant hydration of the non-modified Weck-Cel® following 3 second of water exposure, compared to ALD modified Weck-Cel®.

FIG. 2A shows static CA measurements using a 10 μL water droplet resting on the surface of: non-patterned PDMS (CA=101°) performed at room temperature. FIG. 2B shows 10 μm squared micro-patterned PDMS (CA=164°) performed at room temperature. FIG. 2C shows CA measurements on 3-D porous PDMS (CA=155°) FIG. 2D shows ALD-modified Weck-Cel® (CA=131°). FIG. 2E shows Cassie-Baxter state evaluation by the degree of droplet elongation (increase in AR) following vertically pulling off the surface. The 10 μm patterned PDMS resulted in minimal AR change (1:1), suggestive of minimal water adsorption by the surface. FIG. 2F shows the 40 μm patterned PDMS exhibited increase in the AR of the droplet (from 1.1 to 1.3), suggesting increase in water adsorption by the surface. FIG. 2G shows the 80 μm patterned PDMS exhibited increase in the AR of the droplet (from 1.1 to 1.3), suggesting increase in water adsorption by the surface. FIG. 2F shows the 120 μm patterned PDMS exhibited increase in the AR of the droplet (from 1.1 to 1.3), suggesting increase in water adsorption by the surface.

FIG. 3A shows spreading of a 10 μL droplet of SiO on the surface of the micro-patterned PDMS in air. FIG. 3N shows complete absorption was achieved within 120 seconds following SiO exposure on the surface of ALD-modified Weck-Cel®.

FIG. 4A shows rate of absorption of SiO by ALD-modified Weck-Cel®. FIG. 4B shows standard non-modified commercial Weck-Cel® absorbed SiO at the same rate as ALD-modified Weck-Cel® shown in FIG. 4A. FIG. 4C shows water absorbtion by the ALD modified Weck-Cel®. FIG. 4D shows water absorption by the ALD modified Weck-Cel® was inhibited as compared to the non-modified Weck-Cel®.

FIG. 5A shows serial images of SiO removal (left to right) from IOL in aqueous environment using ALD modified Weck-Cel®. FIG. 5B shows serial images of SiO removal (left to right) from IOL in aqueous environment using 3-D porous PDMS. FIG. 5C shows serial images of SiO removal (left to right) from IOL in aqueous environment using micro-patterned PDMS. Bulk SiO removal was achieved using either the 3-D porous PDMS or the ALD modified Weck-Cel®, and final polishing was accomplished using the micro-patterned PDMS. Contact angle measurements with silicone oil: Series of CA measurements of SiO (10 μL) while spreading on the surface of the micro-patterned PDMS. Each series A-C shows the following: First panel, Droplet placement on the surface (CA=52°), Second panel, 30 seconds later(CA=49°), Third panel, 60 seconds later(CA=29°), and Fourth panel, 120 seconds later(CA=12°).

FIG. 6A shows a series of photographs (left to right) taken during simulated vitrectomy surgery in an explanted porcine eye (left panel). Anterior vitreous removal was performed and an acrylic IOL was implanted in the AC through scleral incision. The eye was filled with SiO followed by BSS exchange (middle panel). Copious irrigation/aspiration was performed to remove residues of SiO from the surface of the IOL and the AC. Small SiO droplets formed on the surface of the IOL (right panel). FIG. 6B shows removal of small SiO droplets formed on the posterior surface of the cornea. Complete removal of SiO droplets was accomplished using the 3-D porous PDMS material that resulted in instantaneous SiO absorption from the surface of the IOL (left and middle panels). Further surgical manipulations resulted in removal of additional SiO droplets, attached to the posterior surface of the cornea (right panel). FIG. 6C shows continued removal of additional SiO droplets attached to the posterior surface of the cornea (left and middle panels). The procedure was performed in approximately 30 seconds and resulted in complete removal of visible SiO from the surface of the IOL and the endothelium (right panel).

DETAILED DESCRIPTION

Definitions

Figure 1A:
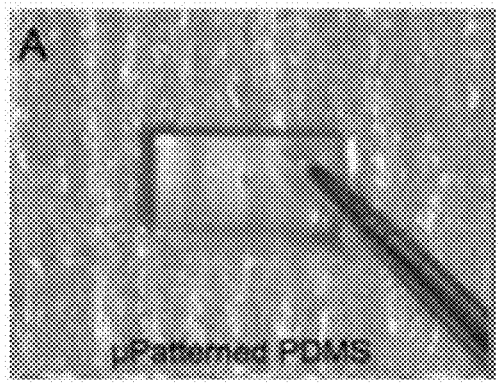
FIGS. 1A-L depict exemplary oleophilic matrixes of the disclosure.
Figure 1D:
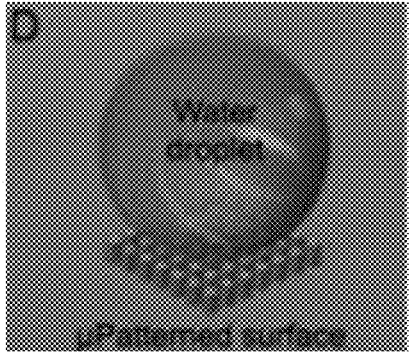
Figure 1B:
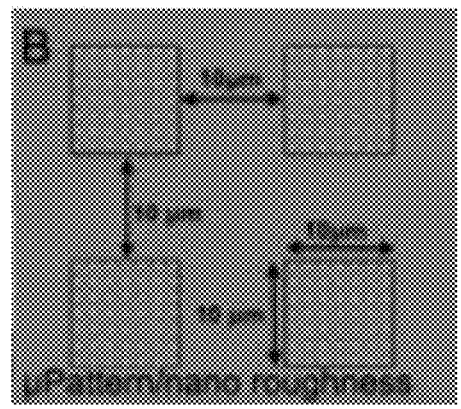

As used herein, "micropillars" refers to microscopic columns. Such columns can be fabricated by, for example, soft lithography techniques and deposited onto surfaces. The size of the micropillar is determined by parameters in one dimension. For instance, a micropillar column having a size of 10 μm has linear dimensions of 10 μm (length)×10 μm (width), and can be, e.g., 25 μm in height. In some embodiments, the micropillars have a size in a range of about 1 μm to about 1000 μm. In some embodiments, the micropillars have a size in a range of about 0.5 μm to about 120 μm. In some embodiments, the micropillars have a size in a range of about 10 μm to about 120 μm. For example, the micropillar can have a size of about 10, about 40, about 80, or about 120 μm. In general, micropillars useful in the present compositions have a high-aspect ratio, i.e., they exhibit a high ratio of height vs. width.

As used herein, "micropore" or "microporous" refers to microscopic holes. The micropores can be fabricated with a negative template, for example, using water-soluble microparticles that can be dissolved in water and thereby removed after the fabrication process; in some embodiments, sucrose particles are used. In another non-limiting example, polystyrene or poly-(methyl methacrylate) particles can be used, and subsequently dissolved by heat treatment. The size of the micropores is determined by the diameter of the particles. In some embodiments, the micropores have a size in a range of about 0.5 µm to about 500 µm. In some embodiments, the micropores have a size in a range of about 10 µm to about 500 µm. In some embodiments, the micropores have a size in a range of about 100 µm to about 300 µm. For example, the micropores can have a size of about 100, about 200, or about 300 µm.

As used herein, "ophthalmic-grade cellulose" refers to biocompatible cellulose materials suitable for ophthalmic uses, for example, eye surgery. Such products are often used in eye surgical fluid control, are made from highly absorbent, natural cellulose material, and are designed for use in small surgical areas. Characteristics of an ophthalmic-grade cellulose include the maintenance of rigidity during the wicking process. Examples of an ophthalmic-grade cellulose include Weck-Cel® Cellulose Fluid Control Products (Beaver-Vistec International), Pro-ophta® (Lohmann & Rauscher), and Sugi® (Kettenbach GmbH & Co. KG).

As used herein, an "alumina-deposited surface" is a layer of alumina that has been placed on the surface of a material, e.g., the surface of a polymer, e.g., by thin-film deposition techniques. For example, the thin-film deposition technique can be atomic layer deposition (ALD), which is based on the sequential use of a gas phase chemical process. In the case of alumina, the chemical process can be, e.g., the reaction of trimethylaluminum and water precursors to produce $Al_2O_3$. These precursors react with the surface of a material one at a time in a sequential, self-limiting, manner. Through the repeated exposure to separate precursors, a thin film is slowly deposited. Sequential cycles can be used to create multiple layers of the alumina-deposited surface. In some embodiments, the alumina-deposited surface has a thickness in a range from about 1.0 to about 2.0 angstroms/cycle. In some embodiments, the alumina-deposited surface has a thickness in a range from about 1.2 to about 1.3 angstroms/cycle. In some embodiments, the number of cycles range from about 1 to about 7. For example, the number of cycles can be 1, 2, 3, 4, 5, 6, or 7. The final thickness of the resulting alumina-deposited surface can be in a range from about 2 to about 14 angstroms. In some embodiments, the final thickness of the alumina-deposited surface is in a range from about 1.2 to about 9.1 angstroms.

Design and Fabrication of a Oleophilic Matrix

Previous attempts to remove silicone oil (SiO) from intraocular lenses (IOLs) have been difficult due to the strong interaction between the SiO and the IOLs, potentially due to their hydrophobic nature. The use of fluorinated solvents[7] to remove SiO can have toxic effects intraocularly, since they do not remove SiO but rather form a solution that is dispersed in the eye. Viscoelastic substances on the other hand, such as Healon, are non-toxic intraocularly, but have had limited success.[1-6]

Achieving SiO removal from IOLs requires consideration of the thermodynamic interactions that take place between SiO and IOL material. In general, the degree of mixing of two fluids is favored by entropy, but also depends on the enthalpies of mixing. Thus, two non-polar substances may not mix when the enthalpic disadvantage outweighs the entropic advantage of mixing, as described in the following formula:

$$\Delta G_{mixing} = \Delta H_{mixing} - T\Delta S_{mixing}$$

where $\Delta H_{mixing} = 2\Delta H_{a-b} - \Delta H_{a-a} - \Delta H_{b-b}$ and a and b are the two fluids.

However, the inability of hydrophobic compounds to mix with water cannot be explained by the low enthalpic and high entropic behavior of such systems. In hydrophobic interactions, entropy favors de-mixing instead of mixing, which is a consequence of the conformational entropy of water molecules. Hydrogen molecules have the freedom to make bonds with their nearest neighbors. Replacing one water molecule with a molecule of a hydrophobic solvent reduces the conformational entropy from six possible bonds to three. Thus, this 50% reduction in the conformational entropy of the system results in an energy penalty that favors de-mixing. The clustering of SiO in water is not due to molecular attraction, but rather an attempt to minimize the conformational entropy loss by surface minimization.

Based on this physical analysis, new oleophilic matrixes to remove SiO in aqueous environments were fabricated. Several micro engineering techniques were employed to accomplish this task, including soft lithography and atomic layer deposition (ALD), resulting to the fabrication of three different materials characterized by enhanced hydrophobicity and oleophilicity. By measuring the liquid/vapor interface that meets the solid surface, the hydrophobic/hydrophilic behavior of each matrix was determined. Likewise, the Cassie-Baxter state was also assessed using contact angle (CA) and AR (elongation of the water droplet, as determined in FIG. 2) measurements. The Cassie-Baxter state describes the ability of a surface to prohibit water molecules from penetrating into the grooves. This allows effortless spreading of SiO in aqueous environments. The dynamic CA and AR measurements showed that the micropatterned PDMS possess such properties.

Provided in this disclosure are polydimethylsiloxane (PDMS) and Weck-Cel® polymers modified to exhibit oleophilic and hydrophobic properties. Both materials are biocompatible and FDA approved for surgical use.[14] In particular, PDMS is used for the packaging of implantable biomedical micro-devices and sensors,[8,9] for fabrication of implantable glaucoma valves,[10] for designing drug-eluting scaffolds[11,12] and epiretinal implantable electrodes, and in the synthesis of new composite injectable cement.[13] Similarly, atomic layer deposition of $Al_2O_3$ is used as a coating technique in bio-MEMS and other devices that come into contact with biological media,[15] scaffold for osteointegration,[16,17] and bone prosthesis.[18] It is reported to be as biocompatible as glass,[15] with good bone tissue compatibility.[18] Weck-Cel® sponges are the standard in eye surgical fluid control, made of highly absorbent, natural cellulose material, and are biocompatible and safe for use in delicate surgical areas. Appropriate sterilization may be required to ensure the safety of the procedure. For example, PDMS can be sterilized by heat (dry or steam) and ALD modified Weck-Cel® can be sterilized by gamma-irradiation.

All materials demonstrated the ability to absorb SiO. The ALD modified Weck-Cel® absorbed SiO faster that the 3-D porous PDMS. However, the 3-D porous PDMS has advantages in that it is an FDA approved polymer, currently used for retinal tamponade; its fabrication is simple and inexpensive; and it can be fabricated in large scale. Both the 3-D porous PDMS and the ALD modified Weck-Cel® showed increased capacity to remove bulk quantities of SiO, however the super-hydrophobic properties of the micro-patterned PDMS provided detailed removal of even strongly adherent SiO remnants.

Methods of Using the Oleophilic Matrices

Figure 7:
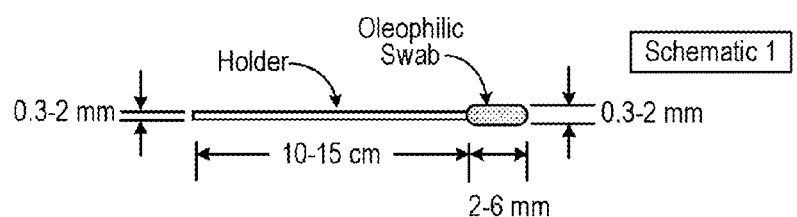
FIG. 7 shows illustrations of several exemplary swab configurations.
Figure 7:
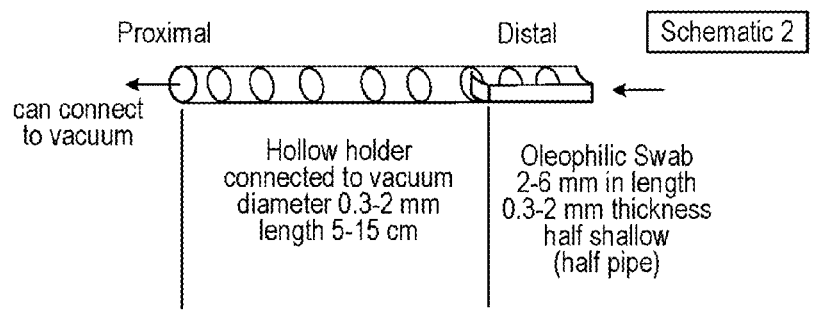
Figure 7:
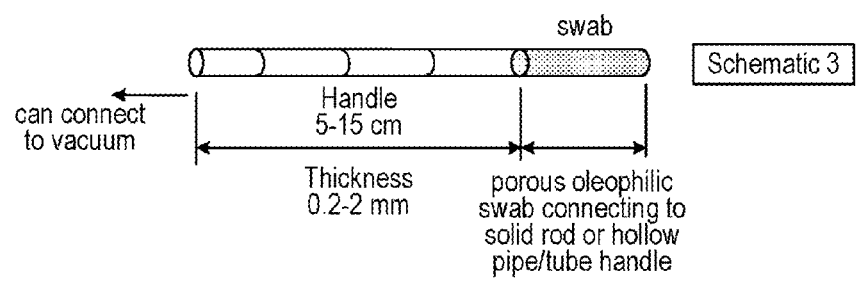

The oleophilic matrixes as described herein can be used, e.g., to remove a hydrophobic fluid, e.g., an oil, such as silicone oil, from a hydrophobic surface such as an intraocular lens. In some embodiments, the removal of oil can be performed by means of a surgical intraocular swab. Such swabs comprise a tip portion and a rigid member. The tip portion comprising an oleophilic matrix as described herein is sized to provide access to the intraocular lens within the eye. The rigid member has a distal end portion and a proximal end portion. The distal end portion of the rigid member is attached to the swab. The proximal end portion comprises a handle for a user to control the movement of the swab. In some embodiments, the handle has a tapered design. The handle can be solid or hollow, and can have various shapes, for example, it can increase in diameter at the proximal edge. A hollow handle can be connected to a vacuum line and be used, for example, to siphon out oil droplets. In some embodiments, the tip portion can be porous to facilitate the siphoning process. The material of the handle can be hydrophobic, and/or hydrophilic material, or mixtures thereof. The swab and/or tip portion thereof can independently be of a hollow pipe, half pipe, tapered edge, solid cylinder, or flat spear configuration. It can be made of different sizes to be inserted through small gauges cannulas, e.g., 27 gauge, 25 gauge, 23 gauge, and 20 gauge. In a non-limiting example, a swab can have a cylindrical handle with a size in a range of about 10 to about 15 cm in length and a diameter in the range of about 0.3 to about 2 mm, with a tip portion in a size range of about 2 to about 6 mm in length and a diameter in the range of about 0.3 to about 2 mm. Some exemplary configurations are shown in FIG. 7.

Further, an oleophilic matrix of the disclosure can have wider industrial applications, for example, retrieval of oil or other hydrophobic liquids from the environment. In some embodiments, the oleophilic matrix can be used to remove oil, such as crude oil, from an aqueous or semi-aqueous environment, such as a naturally-occurring or man-made body of water, e.g., lake, pond, ocean, bay, or sea. For example, the oleophilic matrix can be attached to one or more surfaces on an oil boom or other floating or semi-submerged device, e.g., to contain or to remove crude oil during oil spills in the ocean. In another non-limiting example, the oleophilic matrix may be connected to vacuum tubing to siphon the oil out to containers.

Example 1—Oleophilic Matrixes and Ophthalmic Use

This Example describes the design, fabrication, and evaluation of materials to remove silicone oil (SiO) droplets from intraocular lenses (IOL) during vitreoretinal surgery.

Materials and Methods

Hydrophobic/Oleophilic Materials

Three different materials were designed and fabricated, exhibiting low surface energies and adequate critical surface tension. The first two materials were fabricated using biocompatible polydimethylsiloxane (PDMS), modified by either soft lithography or inverse three-dimensional (3-D) fabrication, while the third material was fabricated using FDA approved surgical Weck-Cel®, precisely modified using atomic layer deposition (ALD) of alumina ($Al_2O_3$). All materials exhibited hydrophobic properties.

1. PDMS surface patterning was performed using standard soft lithography techniques. The objective was to create a PDMS surface with high-aspect ratio micropillars with nano-roughness on their surface with minimum surface energy (FIG. 1A-D).

Figure 8:
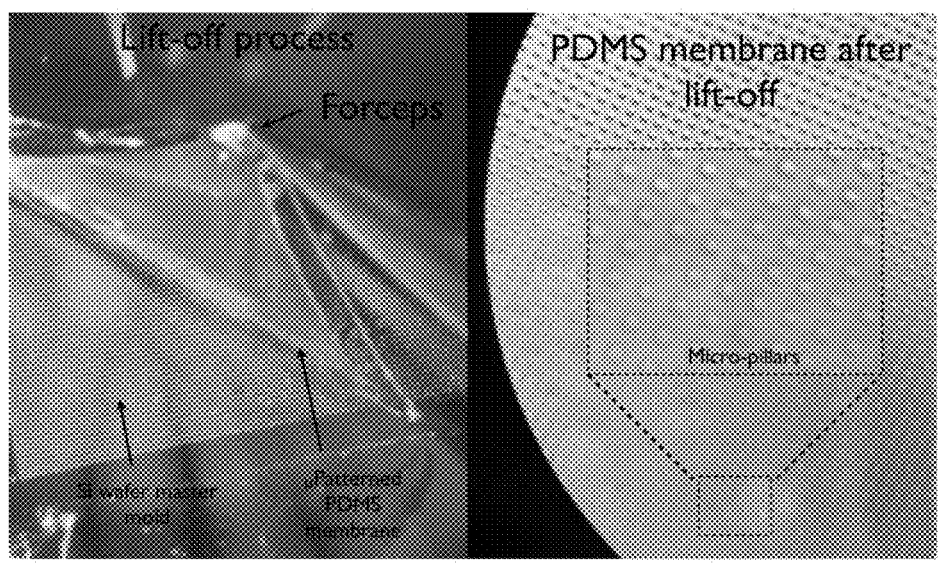
FIG. 8 shows the lift-off process of micropatterned PDMS. SU-8 photoresist was spin coated on a Si wafer and exposed to create a checkerboard pattern. PDMS pre-polymer was then placed on the patterned SU-8, degassed in vacuum for 15 minutes, and cured in 65° C. overnight. Cured PDMS was then removed, resulting in a negative pattern (left). Microscopy examination validated the micropillar pattern (right).

PDMS flexible silicon elastomer was used with a base to curing agent ratio of 10:1 by weight, to prepare the liquid pre-polymer (Sylgard 184, Dow Corning Corporation, Midland, Mich., USA). Further reduction of the surface energy of the PDMS was achieved using soft lithography techniques, and the creation of high-aspect ratio micro-pillars with surface nano-roughness. To achieve this, a master mold was fabricated using permanent epoxy negative photoresist SU-8 (MicroChem corporation, Newton, Mass., USA), as follows: SU-8 3005 was spin-coated on a 3-inch Si wafer (4000 rpm), resulting in 4 μm thickness photo resist. A chrome photomask of 600×600 nm checkerboard patterns, made by electron beam photolithography, was used as UV light blocker. Following UV exposure and SU-8 development, a secondary SU-8 3035 photoresist layer 25 μm in thickness was spin-coated on the same Si wafer. UV light exposure was blocked again using a photomask with square checkerboard features of 10, 20, 40, 80, and 120 square micrometers (FIG. 1). Following SU-8 development, PDMS liquid polymer was poured over, placed in a vacuum chamber for 15 minutes, and then cured by baking at 65° C. overnight. PDMS was then lifted off and manually trimmed to the desired shape and size (FIG. 8).

Figure 1E:
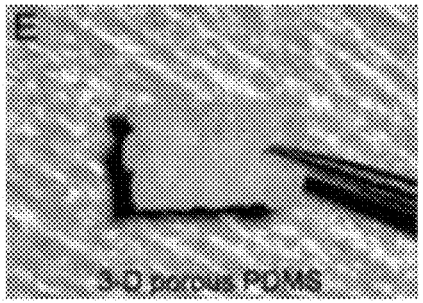
Figure 1C:
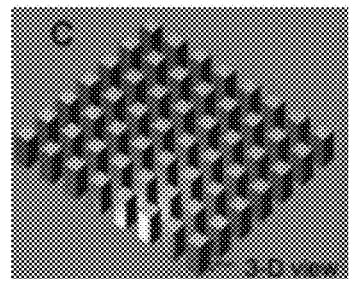
Figure 1F:
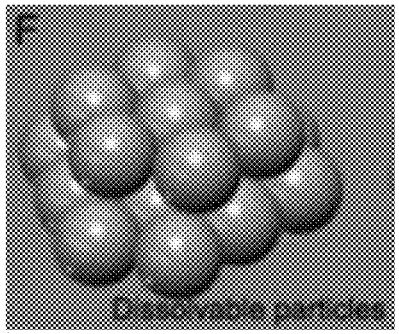
Figure 1G:
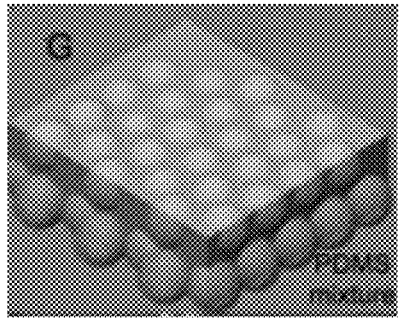
Figure 1H:
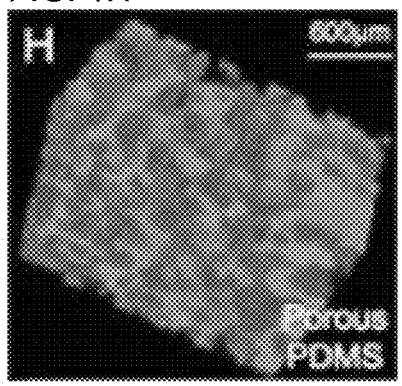
Figure 1I:
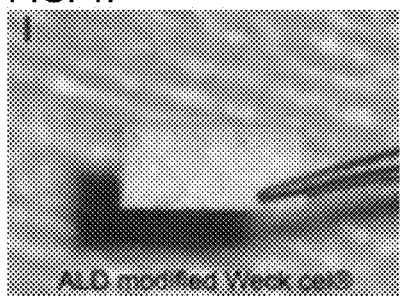
Figure 1J:
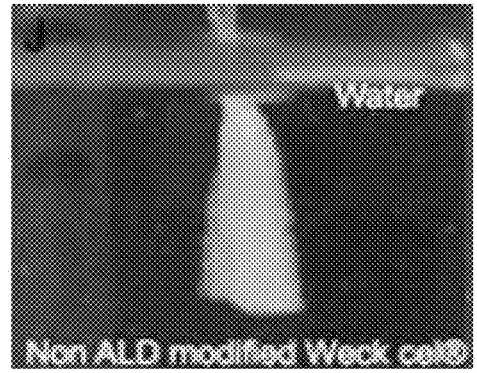
Figure 1K:
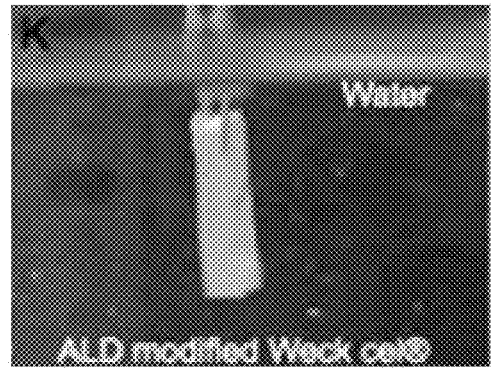
Figure 1L:
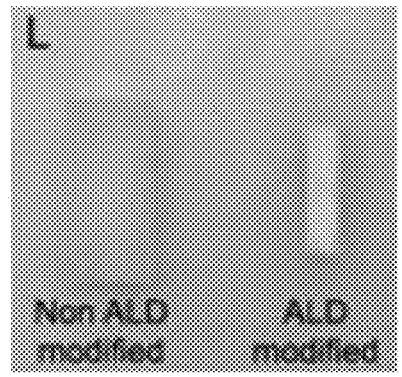

2. Three-dimensional porous PDMS block was fabricated using water dissolvable sucrose micro-particles as a negative template. The size of the particles determined the diameter of the cavitation within the block (FIG. 1E-G). The resulting microporous PDMS was sectioned to smaller segments (3×0.5×3 mm; length×width×height) for surgical use. Using non-destructive x-ray μCT imaging, the porosity of the 3-D PDMS was visualized (FIG. 1H). The analysis showed presence of polydispersed porosity, from 100 to 300 μm in diameter.

3-D porous PDMS block was fabricated using water dissolvable sucrose micro-particles as a negative template. Different sized particles were generated by friction grinding, and size-sorted using a vibrating sieve. Particles of 100, 200, and 300 μm in size were used in equal volumes as a template. Removal of these particles resulted in a PDMS block with interconnected 3-D polydispersed microporosity (FIG. 2). Sucrose was chosen due to its excellent biocompatibility, water solubility, and low cost. In detail, sucrose particles were laid on a 3-inch Si wafer in a petri dish and sonicated for 30 seconds to minimize the dead space. PDMS flexible silicon elastomer, with a base to curing agent ratio of 10:1 by weight, was placed on top of the template in the petri dish, and degassed for 2 hours in the vacuum chamber. The mixture was then cured overnight and the sucrose template was dissolved using water agitation at 95° C. for 3 hours. The porosity of the 3-D PDMS was determined using non-destructive 3-D x-ray micro-computed-tomography (μCT) (X-Tek HMXST225, Nikon Metrology Inc., Brighton, Mich., USA), and 3-D image rendering was performed using software image reconstruction (VGStudio Max 2.2, Heidelberg, Germany). X-rays were generated using a molybdenum target exposed to 70 KV and 140 μA and x-ray scans were radial.

3. Surgical cellulose Weck-Cel® was purchased from BVI (Beaver Visitec International, Waltham, Mass.). Hydrophilic Weck-Cel® was converted to hydrophobic using atomic layer deposition (ALD) of $Al_2O_3$. This modification provided hydrophobic/oleophilic properties to Weck-Cel® (FIG. 1I-L).

Hydrophilic Weck-Cel® was converted to a hydrophobic/oleophilic polymer using ALD of $Al_2O_3$ in a temperature and pressure controlled chamber reactor (Shavana, Cambridge NanoTech, Waltham, Mass.). In detail, trimethylaluminium (TMA) (98%, Chemicals, Inc.) and deionized (DI) water were the precursors for the ALD reaction. $Al_2O_3$ deposition was achieved at 2 Torr pressure by alternating TMA and DI as follows: [TMA/purge/DI/purge]=[0.03/60/5/60 sec]. Hydrophobicity was achieved with ALD cycles as described previously.[5] The temperature throughout the deposition was kept to 100° C., resulting in ~1.2-1.3 angstroms/cycle thickness deposited of $Al_2O_3$, as measured on a planar Si wafer.

Results
Hydrophobicity/Oleophilicity Assessment

Hydrophobicity/oleophilicity was determined by using static contact angle (CA) measurements with 10 μL DI water or SiO in room temperature. Hydrophobicity describes the ability of a surface to repel water and oleophilicity the ability to bind hydrocarbons or SiO. Experimentally, this is assessed by placing a water or SiO droplet on the surface of the materials and measuring the contact angle between the solid-liquid interface. Small contact angles (much less than 90°) correspond to high wettability (oleophilicity or hydrophilicity), while large contact angles (>90° correspond to low wettability (hydrophobicity or oleophobicity). Contact Angles more than 160° are suggestive of super low wettability (super hydrophobicity or super oleophobicity), while CA≈0° responds to super wettability (super hydrophilicity or super oleophilicity).

Figure 2A:
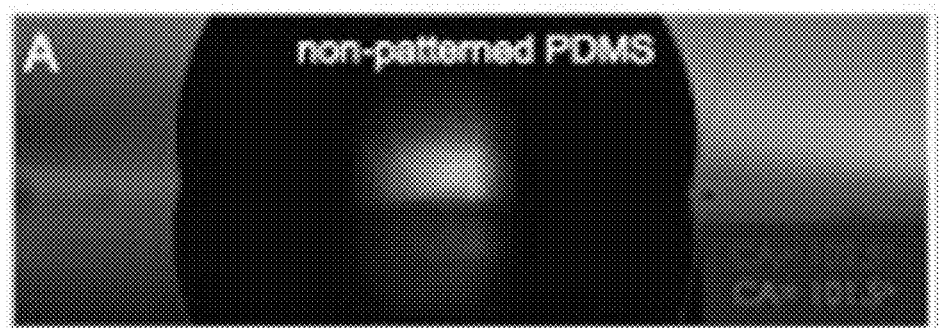
FIGS. 2A-H depict water contact angles of materials.
Figure 2B:
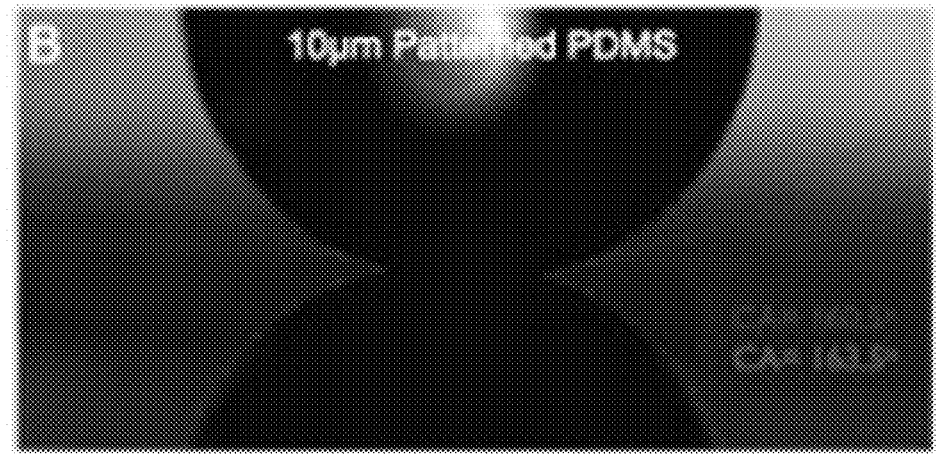
Figure 2C:
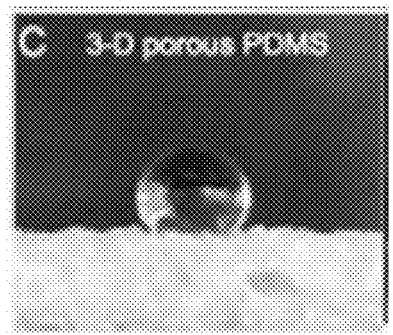
Figure 2D:
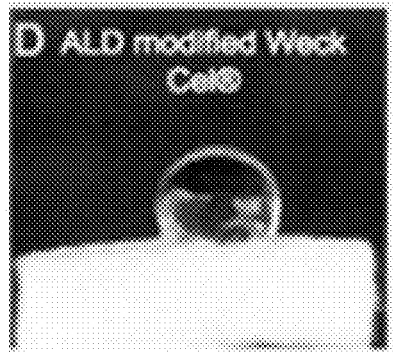
Figure 2E:
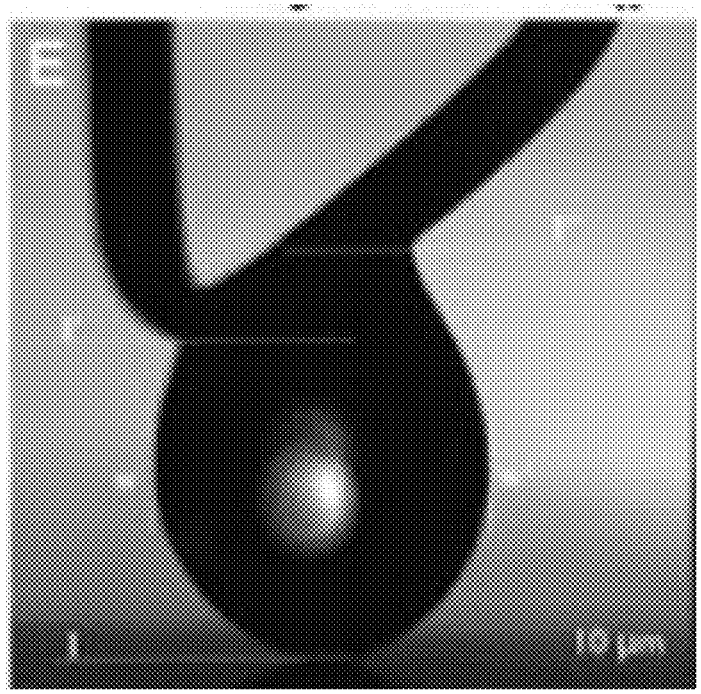
Figure 2F:
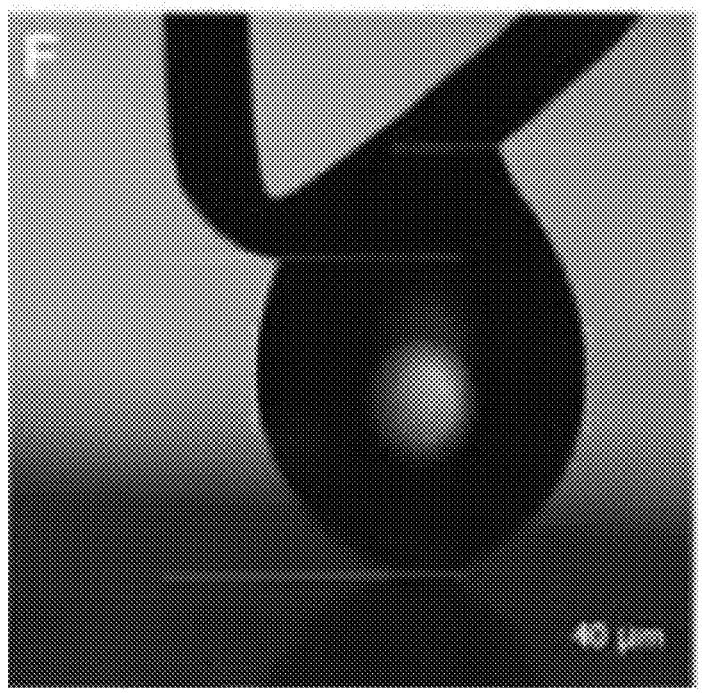
Figure 2G:
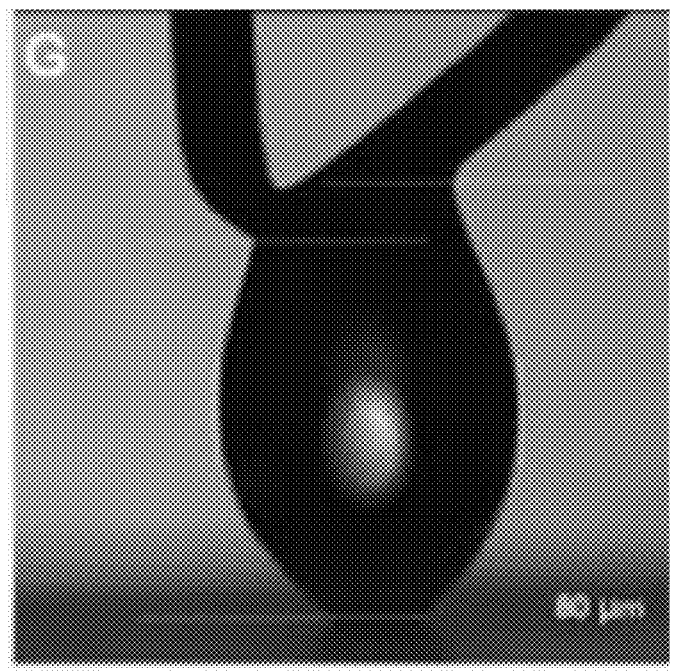
Figure 2H:
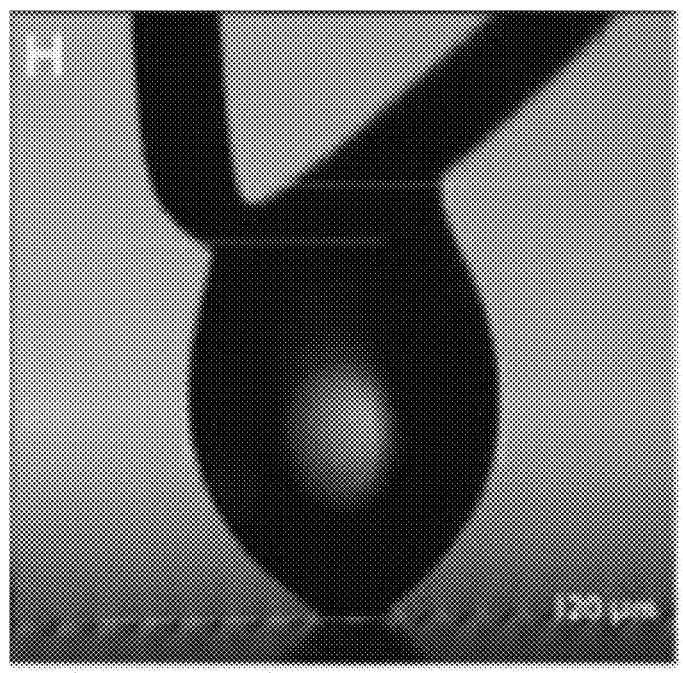
Figure 3A:
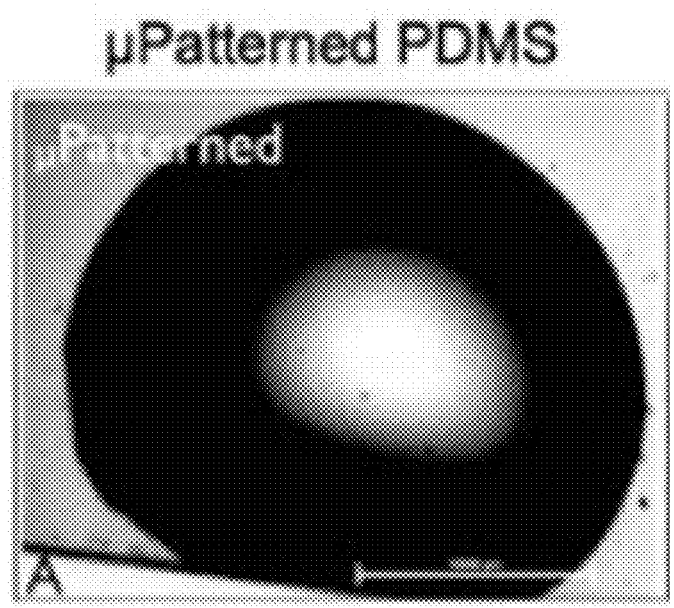
FIGS. 3A-N show SiO (silicone oil) absorption by materials.
Figure 3B:
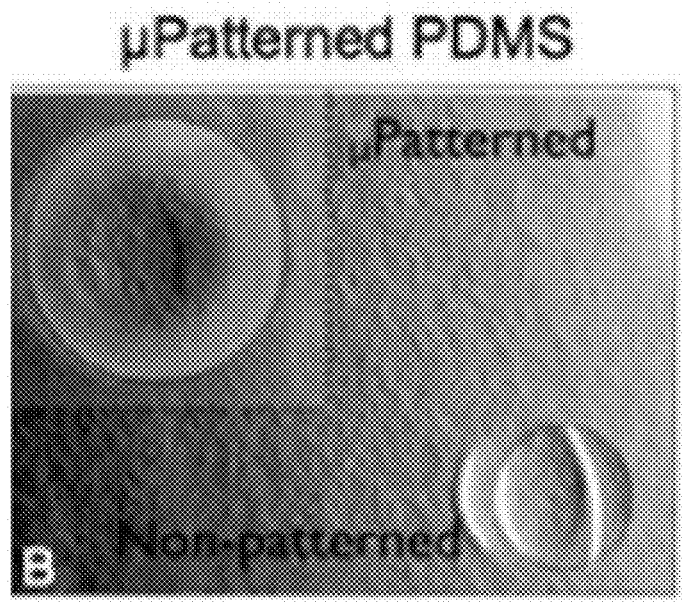
FIG. 3B shows the micro-patterned PDMS resulted in a 358% increase in spreading area as compared to SiO deposited on the surface of non-patterned PDMS.
Figure 3C:
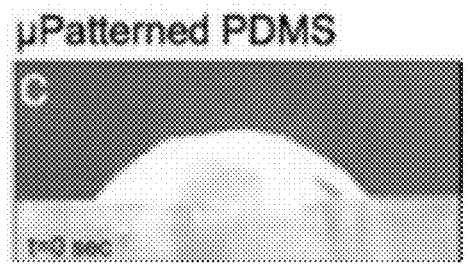
FIG. 3C shows spreading of droplet of SiO on the surface of micro-patterned PDMS at t=0 sec.
Figure 3E:
FIG. 3E shows spreading of droplet of SiO on the surface of micro-patterned PDMS at t between 0-120 sec.
Figure 3D:
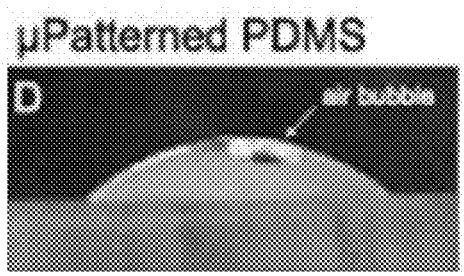
FIG. 3D shows spreading of droplet of SiO on the surface of micro-patterned PDMS at t between 0-120 sec.
Figure 3F:
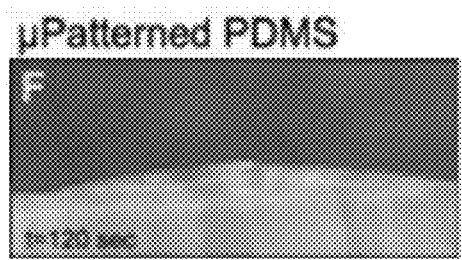
FIG. 3F shows complete spreading was achieved within 120 seconds following SiO exposure on the surface of micro-patterned PDMS and resulted to a contact angle of 12° (oleophilic).
Figure 3G:
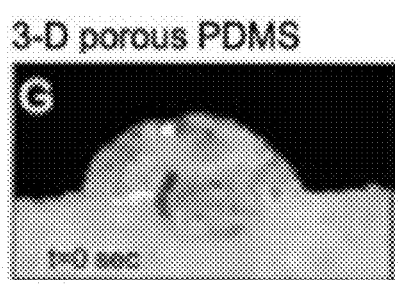
FIG. 3G shows absorption of droplet of SiO on the surface of 3-D porous PDMS at t=0 sec.
Figure 3H:
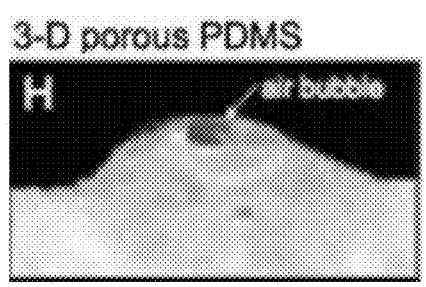
FIG. 3H shows absorption of droplet of SiO on the surface of 3-D porous PDMS at t between 0-120 sec.
Figure 3I:
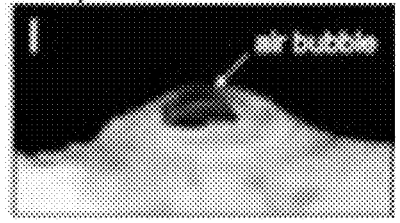
FIG. 3I shows absorption of droplet of SiO on the surface of 3-D porous PDMS at t between 0-120 sec.
Figure 3J:
FIG. 3J shows complete absorption was achieved within 120 seconds following SiO exposure on the surface of 3-D porous PDMS.
Figure 3K:
FIG. 3K shows absorption of droplet of SiO on the surface of ALD-modified Weck-Cel® at t=0 sec.
Figure 3M:
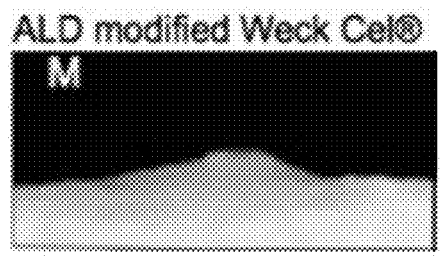
FIG. 3M shows absorption of droplet of SiO on the surface of ALD-modified Weck-Cel® at t between 0-120 sec.
Figure 3L:
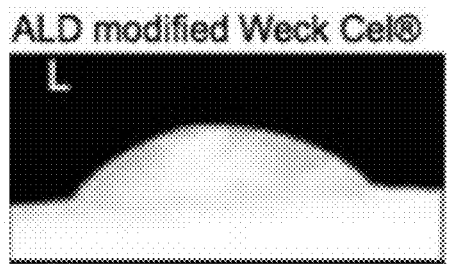
FIG. 3L shows absorption of droplet of SiO on the surface of ALD-modified Weck-Cel® at t between 0-120 sec.
Figure 3N:
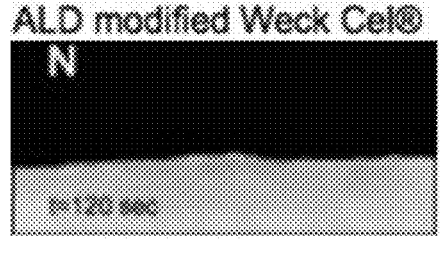

A computer-controlled (CCD) camera (Sony XCD-V50) with green LED background illumination was used to capture images of non-patterned PDMS (FIG. 2A), surface micro-patterned PDMS (FIG. 2B), 3-D porous PDMS (FIG. 2C) and ALD modified Weck-Cel® (FIG. 2D). Static water CA was calculated using drop shape Laplacian analysis (Image J, Wayne Rasband National Institute of Health, USA). Dynamic CA was employed to assess the Cassie-Baxter state of the micro-patterned PDMS. Different pillar sizes were tested (10, 40, 80 and 120 μm) to determine the optimal pillar dimension. Dynamic CA measurements were performed by measuring the elongation of a water droplet subject to vertical pull from the surface of the micro-patterned PDMS (FIG. 2E-H). The following formula was employed to calculate the change in droplet's AR (elongation) before becoming detached from the PDMS surface:

$$AR=(L_{ll'}+L_{ll'}/2)/L_{ww'}$$

In Vitro Assessment

SiO removal from IOLs was performed in vitro as follows: 5 IOLs (2 silicone and 3 acrylic) were submerged in medical grade SiO (SILIKON™ 1000, Alcon Laboratories, Fort Worth, Tex.) for 3 days. They were then removed, and excess oil was removed by balanced salt solution (BSS) irrigation. The IOLs were then placed in a glass beaker (100 ml BSS) for 30 minutes until SiO droplet formation occurred on the IOL surface. SiO removal was then performed using the fabricated materials. SiO removal was assessed based on previously described methods.[6]

Ex Vivo Assessment

Pars plana lensectomy and vitrectomy in explanted porcine eyes was performed using the 23G transconjunctival Accurus vitreotome from Alcon. An acrylic IOL (AcrySof® IQ Aspheric, Alcon, Fort Worth, Tex.) was implanted in the anterior chamber (AC) of the eye, and the posterior segment was filled with SiO 1000 centistoke (Silicon™ 1000, Alcon, Fort Worth, Tex.). The oil was left for several minutes and was subsequently removed and exchanged for BSS (BSS®, Alcon, Fort Worth, Tex. company). Triple irrigation/aspiration cycles were performed to thoroughly remove the SiO. Droplets of SiO remnants formed on the posterior surface of the IOL and the AC, which were removed using a 2 mm wide 3-D porous PDMS material.

In Vitro Assessment of Hydrophobicity/Oleophilicity

Static CA measurements of water or oil are used to determine the hydrophobicity or oleophilicity of surface. Large CA>90° correspond to low wettability (hydrophobicity or oleophobicity). Extremely large CA>160° are suggestive of super low wettability (super hydrophobicity or super oleophobicity), while extremely low CA≈0° responds to super wettability (super hydrophilicity or super oleophilicity).

Provided that SiO and IOL interaction is a highly hydrophobic phenomenon, introducing a more hydrophobic material than the IOL itself can challenge this interaction and preferentially remove the SiO from the surface of the IOL.

Three oleophilic materials (3-D porous PDMS and ALD modified Weck-Cel® and micro-patterned PDMS) were created as described in the Materials and Methods section and shown in FIG. 1. Static CA measurements of the three materials were performed using 10 μL of water. The 3-D porous PDMS and ALD modified Weck-Cel® exhibited CA of 155° and 131°, respectively (FIG. 2B-D)). Increased hydrophobicity/oleophilicity of PDMS was achieved by generating a pillar structure in it surface (FIG. 2A,B), while reducing the pillar size of the pillar structure resulted to increase hydrophobicity. Pillar sizes between 10-40 μm provided super-hydrophobic properties, with static water CAs exceeding >>160° whereas the 80 and 120 μm pillar size exhibited water CA of 145° and 136°, respectively. Dynamic CA measurements using vertical pulling showed a significant 7% reduction in water elongation for each step of pillar size reduction (120, 80, 40, 20, 10 micrometers) demonstrating reduction in water adsorption. The AR of a vertically pulled water droplet was 1:1 for the 10 μm, 1:12 for the 40 μm, 1:35 for the 80 μm, and 1:33 for the 120 μm pillar size (FIG. 2E-H), with the 10 μm pillar size exhibiting the lowest water adsorption.

SiO (10 μL droplet) spreading on the micro-patterned PDMS covered 358% more area than the non-patterned PDMS (FIG. 3A-F). SiO CA measurements on 3-D porous PDMS and ALD modified Weck-Cel® was nearly zero due to oil absorption (FIG. 3G-N). The absorption and spreading rates are presented in Table 1.

Figure 4A:
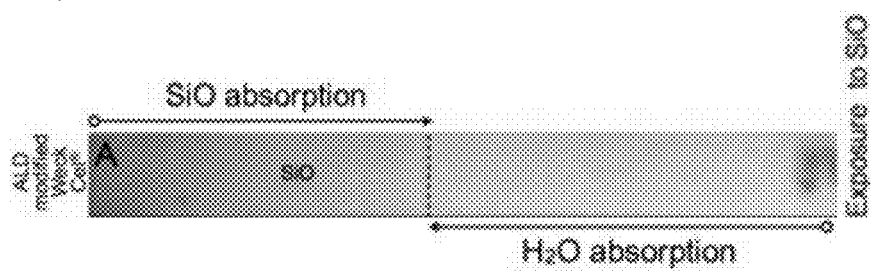
FIGS. 4A-D show SiO and water interaction with modified Weck-Cel®.
Figure 4B:
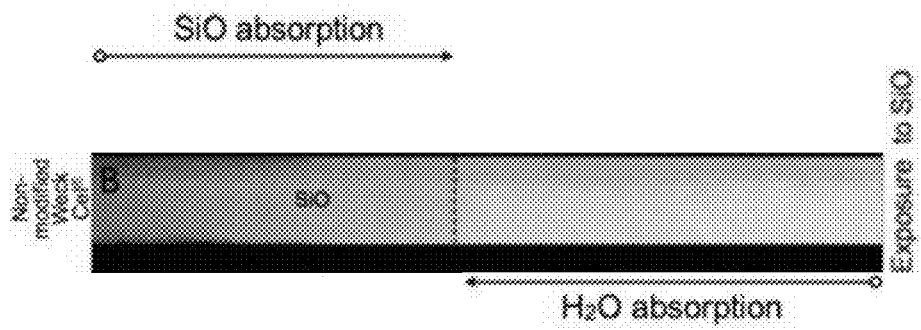
Figure 4C:
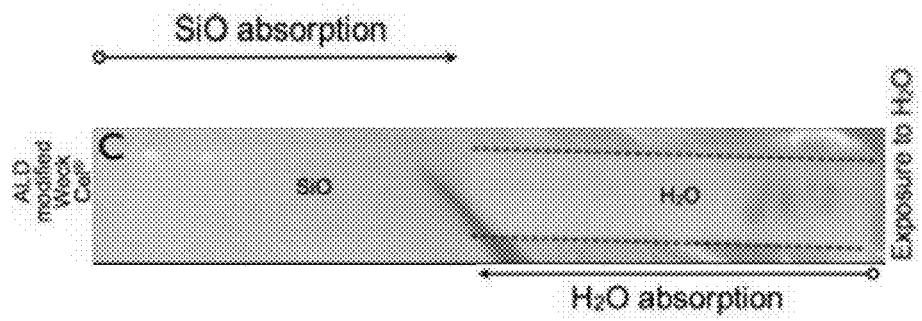
Figure 4D:
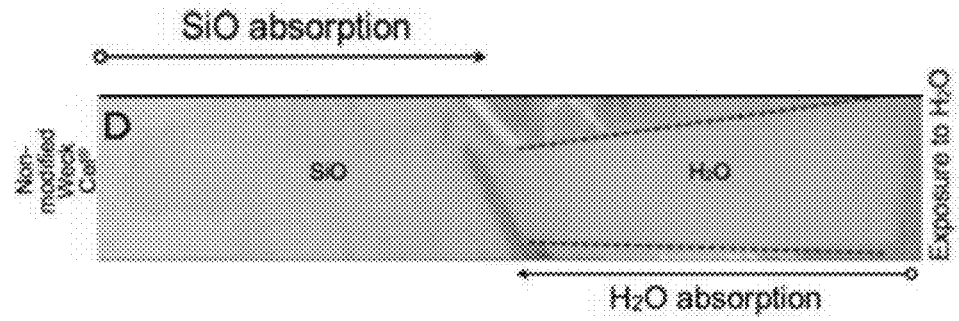

Comparing SiO absorption rate between standard and ALD-modified Weck-Cel®, similar rate were recorded (FIG. 4A,B). However, the ALD modified Weck-Cel® remained dry when submerged in water compared to standard Weck-Cel® that rapidly absorbed water and expanded its volume (FIGS. 1J-L and FIGS. 4C,D)).

TABLE 1

Contact angle measurements in air with 10 μL of PDMS Si oil droplets resting on the surface of micropatterned PDMS, 3-D porous PDMS, and ALD-modified Weck-Cel ®.

| CA measurements using 10 μL of Si oil | micro-patterned PDMS (Spreading) | 3-D porous PDMS (Absorption) | ALD modified Weck-Cel ® (Absorption) |
|---|---|---|---|
| t = 0 sec | 52° | 51° | 56° |
| t = 30 sec | 49° | 45° | 46° |

TABLE 1-continued

Contact angle measurements in air with 10 µL of PDMS Si oil droplets resting on the surface of micropatterned PDMS, 3-D porous PDMS, and ALD-modified Weck-Cel®.

| CA measurements using 10 µL of Si oil | micro-patterned PDMS (Spreading) | 3-D porous PDMS (Absorption) | ALD modified Weck-Cel® (Absorption) |
|---|---|---|---|
| t = 60 sec | 29° | 39° | 12° |
| t = 120 sec | 12° | 0° | 0° |

Both the 3D porous PDMS and the ALD modified Weck-Cel achieve complete oil absorption within 2 minutes form the exposure to Si oil, while the micropatterned PDMS continued the spreading of the Si oil thereafter.

SiO Removal In Vitro

Figure 5A:
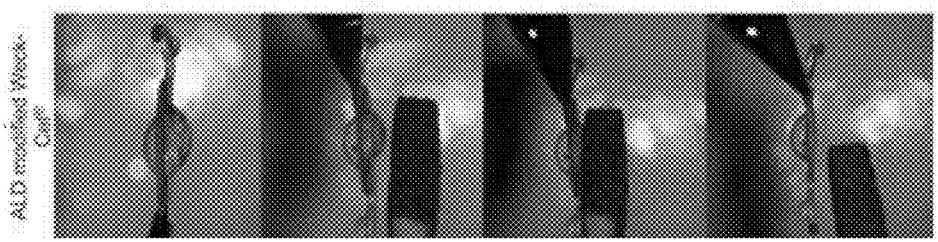
FIGS. 5A-C show SiO removal from IOL in vitro by oleophilic materials.
Figure 5B:
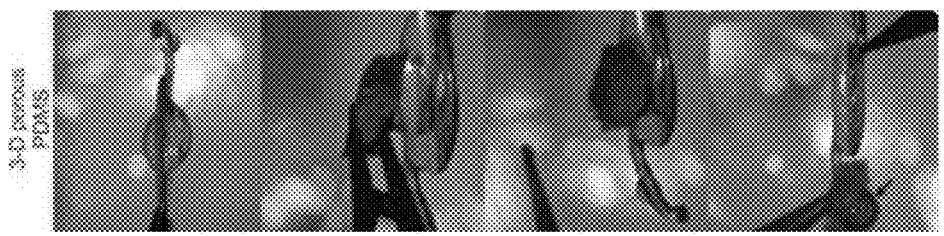
Figure 5C:
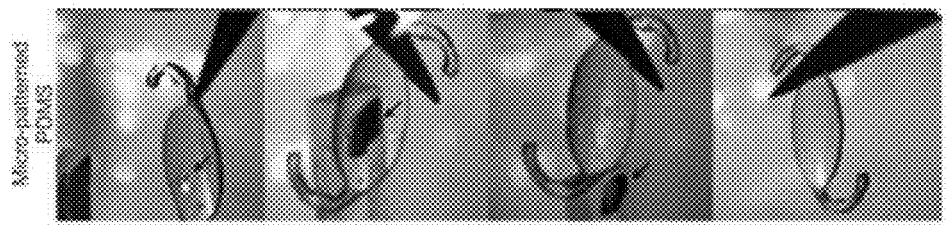

SiO removal from acrylic and silicone IOLs was performed in vitro (FIG. 5I:A and II:A). The 3-D porous PDMS and ALD modified Weck-Cel® were employed first to remove the bulk of the SiO (FIG. 5I:C-D and II:C-D). Remnants of SiO and polishing of the IOL was performed using the micro-patterned PDMS, which is more effective due to its substantially low surface energy, higher CA and thus increased hydrophobicity (FIG. 5III:A-D). SiO removal and polishing of the IOL was accomplished in approximately 2 minutes.

SiO Removal Ex Vivo

Figure 6A:
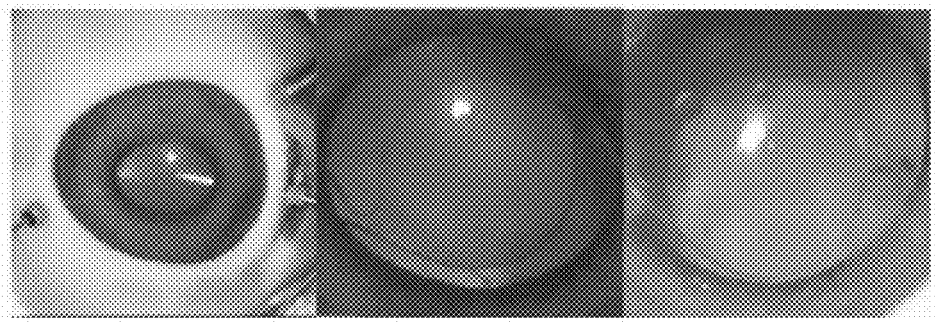
FIGS. 6A-C show SiO removal ex vivo.
Figure 6B:
Figure 6C:
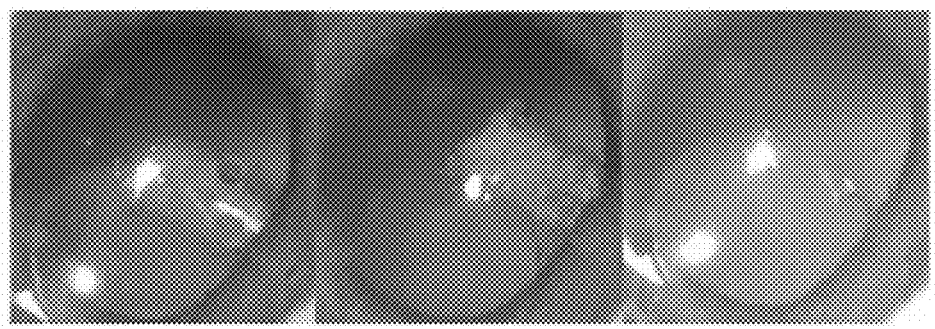

SiO removal was performed ex vivo using a porcine eye. A 23G transconjuctival pars plana vitrectomy, pars plana lensectomy, and acrylic IOL implantation (in AC) were performed. SiO infusion was performed after fluid-air exchange. The oil was left for several minutes, then was subsequently removed and exchanged for BSS (BSS®, Alcon, Fort Worth, Tex. company). Several (three) irrigation/aspiration cycles were performed to thoroughly remove the oil. Nevertheless, remnants of SiO droplets formed on the posterior surface of the IOL and several droplets remained in the AC. The 3-D porous PDMS material (3 mm wide stick) was used to remove SiO droplets from the surface of an acrylic IOL implanted in the in the anterior chamber of the eye (FIG. 6). SiO removal was accomplished in approximately 30 seconds. Floating oil droplets in the anterior chamber and on the posterior surface of the cornea were also removed easily and without complications.

REFERENCES

1. Apple D J, Federman J L, Krolicki T J, et al. Irreversible silicone oil adhesion to silicone intraocular lenses. A clinicopathologic analysis. *OPHTHA.* 1996; 103(10): 1555-61—discussion 1561-2.
2. Stappler T, Williams R, Wong D. F4H5: a novel substance for the removal of silicone oil from intraocular lenses. *British Journal of Ophthalmology.* 2010; 94(3):364-367.
3. Kusaka S, Kodama T, Ohashi Y. Condensation of silicone oil on the posterior surface of a silicone intraocular lens during vitrectomy. *AJOPHT* 1996; 121(5):574-575.
4. Stolba U, Binder S, Velikay M, Wedrich A. Intraocular silicone lenses in silicone oil: an experimental study. *Graefes Arch Clin Exp Ophthalmol.* 1996; 234(1):55-57.
5. Lee K, Jur J S, Kim D H, Parsons G N. Mechanisms for hydrophilic/hydrophobic wetting transitions on cellulose cotton fibers coated using $Al_2O_3$ atomic layer deposition. *J Vac Sci Technol A.* 2012; 30(1):01A163.
6. Apple D J, Isaacs R T, Kent D G, et al. Silicone oil adhesion to intraocular lenses: an experimental study comparing various biomaterials. *Journal of Cartaract & Refractive Surgery.* 1997; 23(4):536-544.
7. Langefeld S, Kirchhof B, Meinert H, Roy T, Aretz A, Schrage N F. A new way of removing silicone oil from the surface of silicone intraocular lenses. *Graefes Arch Clin Exp Ophthalmol.* 1999; 237(3):201-206.
8. Lachhman S, Zorman C A, Ko W H. Multi-layered poly-dimethylsiloxane as a non-hermetic packaging material for medical MEMS. *Conf Proc IEEE Eng Med Biol Soc.* 2012; 2012:1655-1658.
9. Walter P, Schnakenberg U, Bögel Vom G, et al. Development of a completely encapsulated intraocular pressure sensor. *Ophthalmic Res.* 2000; 32(6):278-284.
10. Paschalis E I, Chodosh J, Sperling R A, Salvador-Culla B, Dohlman C. A Novel Implantable Glaucoma Valve Using Ferrofluid. *PLoS ONE.* 2013; 8(6):e67404.
11. Williams D L, Sinclair K D, Jeyapalina S, Bloebaum R D. Characterization of a novel active release coating to prevent biofilm implant-related infections. *Journal of Biomedical Materials Research Part B: Applied Biomaterials.* 2013; 101B (6): 1078-1089.
12. Fischer S, Carstesen D, Klee D, Walter P, Weinberger A W A. Surface-modified silicone foils for intraocular implantation. *Graefes Arch Clin Exp Ophthalmol.* 2012; 250(6):823-827.
13. Ignjatović N, Jovanović J, Suljovrujić E, Uskoković D. Injectable polydimethylsiloxane-hydroxyapatite composite cement. *Biomed Mater Eng.* 2003; 13(4):401-410.
14. Williams R L, Kearns V R, Lo A C, et al. Novel Heavy Tamponade for Vitreoretinal Surgery. *Invest Ophthalmol Vis Sci.* 2013; 54(12):7284-7292.
15. Finch D S, Oreskovic T, Ramadurai K, Herrmann C F, George S M, Mahaj an R L. Biocompatibility of atomic layer-deposited alumina thin films. *J Biomed Mater Res A.* 2008; 87(1): 100-106.
16. Kido H W, Ribeiro D A, de Oliveira P, et al. Biocompatibility of a porous alumina ceramic scaffold coated with hydroxyapatite and bioglass. *J Biomed Mater Res A.* 2013.
17. Dong Z, Wu Y, Wang Q, Xie C, Ren Y, Clark R L. Reinforcement of electrospun membranes using nanoscale $Al_2O_3$ whiskers for improved tissue scaffolds. *J Biomed Mater Res A.* 2012; 100A(4):903-910.
18. Ogihara N, Usui Y, Aoki K, et al. Biocompatibility and bone tissue compatibility of alumina ceramics reinforced with carbon nanotubes. *Nanomedicine (Loud).* 2012; 7(7): 981-993.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A swab comprising a tip portion and a rigid member, wherein the tip portion comprises an oleophilic matrix comprising at least one polymer selected from the group consisting of a polydimethylsiloxane having micropillars; a microporous polydimethylsiloxane; and an ophthalmic-grade cellulose having an alumina-deposited surface.

2. The swab of claim 1, wherein the at least one polymer is a polydimethylsiloxane having micropillars.

3. The swab of claim 2, wherein the micropillars have either length or width in a range from about 0.5 μm to about 120 μm.

4. The swab of claim 3, wherein the micropillars have either length or width of about 10 μm.

5. The swab of claim 3, wherein the micropillars have either length or width of about 40 μm.

6. The swab of claim 3, wherein the micropillars have either length or width of about 80 μm.

7. The swab of claim 3, wherein the micropillars have either length or width of about 120 μm.

8. The swab of claim 1, wherein the at least one polymer is a microporous polydimethylsiloxane.

9. The swab of claim 8, wherein the micropores of the microporous polydimethylsiloxane have a size in a range from about 0.5 μm to about 500 μm.

10. The swab of claim 9, wherein the micropores of the microporous polydimethylsiloxane have a size of about 100 μm.

11. The swab of claim 9, wherein the micropores of the microporous polydimethylsiloxane have a size of about 200 μm.

12. The swab of claim 9, wherein the micropores of the microporous polydimethylsiloxane have a size of about 300 μm.

13. The swab of claim 1, wherein the polymer is an ophthalmic-grade cellulose having an alumina-deposited surface.

14. The swab of claim 13, wherein the alumina-deposited surface was formed by atomic layer deposition.

15. The swab of claim 14, wherein the alumina-deposited surface has a thickness in a range from about 2 to about 14 angstroms.

16. A method for removing an oil from an intraocular lens, the method comprising:
    (a) contacting the oil with a swab of claim 1;
    (b) absorbing the oil onto the oleophilic matrix of the tip portion of the swab; and
    (c) withdrawing the oleophilic matrix to remove the oil from the intraocular lens.

17. The method of claim 16, wherein the oil is a silicone oil.

18. A method for removing an oil from an aqueous medium, the method comprising:
    (a) contacting the oil with a swab of claim 1;
    (b) absorbing the oil onto the oleophilic matrix of the tip portion of the swab; and
    (c) withdrawing the oleophilic matrix to remove the oil from the aqueous medium.

19. The method of claim 18, wherein the aqueous medium is a naturally-occurring or man-made body of water.

* * * * *

UNITED STATES PATENT AND TRADEMARK OFFICE
CERTIFICATE OF CORRECTION

PATENT NO. : 9,999,553 B2
APPLICATION NO. : 14/850537
DATED : June 19, 2018
INVENTOR(S) : Eleftherios Ilios Paschalis and Demetrios Vavvas It is certified that error appears in the above-identified patent and that said Letters Patent is hereby corrected as shown below:

On the Title Page

Item (57) (ABSTRACT), delete "The matrixes can be used," and insert --The matrices can be used,--

Signed and Sealed this
Fifth Day of March, 2019

Andrei Iancu
*Director of the United States Patent and Trademark Office*